United States Patent
Hallinan et al.

(10) Patent No.: US 7,345,197 B1
(45) Date of Patent: Mar. 18, 2008

(54) PREPARATION OF ACETIC ACID

(75) Inventors: Noel C. Hallinan, Loveland, OH (US); Brian A. Salisbury, Oxford, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 11/810,167

(22) Filed: Jun. 5, 2007

(51) Int. Cl.
  *C07C 51/12* (2006.01)
  *C07C 51/14* (2006.01)
  *C07C 51/42* (2006.01)
  *C07C 53/10* (2006.01)
  *C07C 45/78* (2006.01)

(52) U.S. Cl. ............... 562/519; 563/520; 563/607; 563/608; 568/492

(58) Field of Classification Search .............. None
  See application file for complete search history.

(56) References Cited

U.S. PATENT DOCUMENTS

| | | | |
|---|---|---|---|
| 5,620,567 A | 4/1997 | Seidel et al. | |
| 5,817,869 A | 10/1998 | Hinnenkamp et al. | 562/519 |
| 5,932,764 A | 8/1999 | Morris et al. | 562/519 |
| 6,667,418 B2 | 12/2003 | Broussard et al. | 562/519 |
| 7,208,625 B1 | 4/2007 | Wang et al. | 562/608 |

*Primary Examiner*—Sikarl A. Witherspoon
(74) *Attorney, Agent, or Firm*—Shao-Hua Guo

(57) ABSTRACT

A method for removing aldehyde impurities from acetic acid is disclosed. The method comprises extracting the aldehyde impurities from a methyl iodide solution such as the decanter heavy phase with a polyol. After the aldehyde impurities are removed, the methyl iodide heavy phase can be recycled to the carbonylation.

17 Claims, No Drawings

PREPARATION OF ACETIC ACID

FIELD OF THE INVENTION

The invention relates to the preparation of acetic acid. More particularly, the invention relates to a method for removing aldehyde impurities from acetic acid.

BACKGROUND OF THE INVENTION

The carbonylation of methanol produces acetic acid:

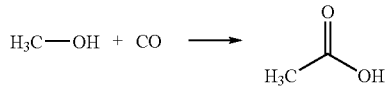

Prior to 1970, acetic acid was made using cobalt catalyst. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One problem associated with the original Monsanto process is that a large amount of water (about 14%) is needed to produce hydrogen in the reactor via the water-gas shift reaction ($CO+H_2O \rightleftharpoons CO_2+H_2$). Water and hydrogen are needed to react with precipitated Rh(III) and inactive [$RhI_4(CO)_2$] to regenerate the active Rh(I) catalyst. This large amount of water increases the amount of hydrogen iodide, which is highly corrosive and leads to engineering problems. Further, removing a large amount of water from the acetic acid product is costly.

In the late '70s Celanese modified the Monsanto process by adding lithium iodide salt to the carbonylation. Lithium iodide salt increases the catalyst stability by minimizing the side reactions that produce inactive Rh(III) species and therefore the amount of water needed is reduced. However, the high concentration of lithium iodide salt promotes stress crack corrosion of the reactor vessels. Furthermore, the use of iodide salts increases the iodide impurities in the acetic acid product.

In the late '90s, Millennium Petrochemical Company developed a new rhodium carbonylation catalyst system that does not use iodide salt. The catalyst system uses a pentavalent Group VA oxide such as triphenylphosphine oxide as a catalyst stabilizer. The Millennium catalyst system not only reduces the amount of water needed but also increases the carbonylation rate and acetic acid yield. See U.S. Pat. No. 5,817,869.

One challenge still facing the industry is that lowering water concentration in the methanol carbonylation results in increased aldehyde formation. Methods for reducing aldehyde concentration in acetic acid are known. For instance, U.S. Pat. No. 6,667,418 discloses a method for reducing aldehydes by oxidizing them with air, hydrogen peroxide and other free radical initiators in an integrated acetic acid production process at an elevated temperature. Introducing free radical initiators into an acetic acid production process is inconvenient.

U.S. Pat. No. 7,208,625 teaches a method for removing aldehyde and other permanganate-reducing impurities from an acetic acid product. The method comprises contacting an acetic acid product containing permanganate-reducing impurities with peracetic acid and an oxygen-containing gas. The method is particularly suitable for post treatment of acetic acid that contains permanganate-reducing impurities. Because the peroxide is not used in the integrated acetic acid production process, its handling is relatively safe and convenient.

Co-pending application Ser. Nos. 11/496,900 and 11/508,109 disclose methods of removing aldehyde impurities from acetic acid by reacting aldehyde with hydroxyl compounds to form corresponding acetals. The acetals are subsequently removed from acetic acid by distillation.

New methods for reducing aldehydes in acetic acid are needed. Ideally, the methods are performed conveniently and safely.

SUMMARY OF THE INVENTION

The invention is a method for removing aldehyde impurities from acetic acid. The method comprises extracting aldehyde from a methyl iodide solution with a polyol. The methyl iodide solution is preferably a decanter heavy phase from the methanol carbonylation. Compared with the methods disclosed in co-pending application Ser. Nos. 11/496,900 and 11/508,109 in which aldehyde reacts with a hydroxyl compound to form corresponding acetal, the method of this invention is surprisingly simple and effective given that the aldehyde is physically extracted by, rather than reacted with, the polyol.

DETAILED DESCRIPTION OF THE INVENTION

Aldehyde impurities are produced by methanol carbonylation. Examples of aldehyde impurities include acetaldehyde, crotonaldehyde, butyraldehyde, their derivatives such as 2-ethyl crotonaldehyde, 2-ethyl butyraldehyde, the like, and mixtures thereof.

The carbonylation reaction is usually performed in the presence of a carbonylation catalyst and a catalyst stabilizer. Suitable carbonylation catalysts include those known in the acetic acid industry. Examples of suitable carbonylation catalysts include rhodium catalysts and iridium catalysts.

Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof.

Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(Co)_2I_2]^-H^+$, $[Ir(CH_3)I_3(CO)_2]^-H^+$, $Ir_4(CO)_{12}$, $IrCl_3.4H_2O$, $IrBr_3.4H_2O$, $Ir_3(CO)_{12}$, $Ir_2O_3$, $IrO_2$, $Ir(acac)(CO)_2$, $Ir(acac)_3$, $Ir(OAc)_3$, $[Ir_{30}(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are acetates.

Preferably, the reaction is performed in the presence of a catalyst stabilizer. Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817,869. Phosphine oxides are more preferred. Triphenylphosphine oxides are most preferred.

The carbonylation reaction is preferably performed in the presence of water. Preferably, the concentration of water present is from about 2 wt % to about 14 wt % based on the total weight of the reaction medium. More preferably, the water concentration is from about 2 wt % to about 10 wt %. Most preferably, the water concentration is from about 4 wt % to about 8 wt %.

The reaction is preferably performed in the presence of methyl acetate. Methyl acetate can be formed in situ. If desirable, methyl acetate can be added as a starting material to the reaction mixture. Preferably, the concentration of methyl acetate is from about 2 wt % to about 20 wt % based on the total weight of the reaction medium. More preferably, the concentration of methyl acetate is from about 2 wt % to about 16 wt %. Most preferably, the concentration of methyl acetate is from about 2 wt % to about 8 wt %. Alternatively, methyl acetate or a mixture of methyl acetate and methanol from byproduct streams of the hydroysis/methanolysis of polyvinyl acetate can be used for the carbonylation reaction.

The reaction is performed in the presence of methyl iodide. Methyl iodide is a catalyst promoter. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Hydrogen may also be fed into the reactor. Addition of hydrogen can enhance the carbonylation efficiency. Preferably, the concentration of hydrogen is from about 0.1 mol % to about 5 mol % of carbon monoxide in the reactor. More preferably, the concentration of hydrogen is from about 0.3 mol % to about 3 mol % of carbon monoxide in the reactor.

Methanol and carbon monoxide are fed to the carbonylation reactor. The methanol feed to the carbonylation reaction can come from a syngas-methanol facility or any other source. Methanol does not react directly with carbon monoxide to form acetic acid. It is converted to methyl iodide by the hydrogen iodide present in the acetic reactor and then reacts with carbon monoxide and water to give acetic acid and regenerate the hydrogen iodide. Carbon monoxide not only becomes part of the acetic acid molecule, but it also plays an important role in the formation and stability of the active catalyst.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 2,000 psig. More preferably, the reaction is performed under a pressure within the range of about 300 psig to about 500 psig.

An acetic acid product stream is usually withdrawn from the reactor and is separated, by a flash separation, into a liquid fraction comprising the catalyst and the catalyst stabilizer and a vapor fraction comprising the acetic acid product, the reactants, water, methyl iodide, and impurities generated during the carbonylation reaction including aldehydes. The liquid fraction is then recycled to the carbonylation reactor. The vapor fraction is then passed to a distillation column.

The distillation column, the so called "light ends distillation," separates an overhead comprising methyl iodide, water, methanol, methyl acetate, and impurities including aldehyde impurities from an acetic acid stream comprising acetic acid, a small amount of water, and heavy impurities. The acetic acid stream may be passed to a drying column to remove water and then be subjected to distillation, so called "heavy ends distillation," to remove the heavy impurities such as propionic acid.

The overhead stream from the light ends distillation preferably comprises from about 60 wt % to about 90 wt % of methyl iodide, from about 5 wt % to about 15 wt % of methyl acetate, from about 1 wt % to about 10 wt % of acetic acid, 1 wt % or less of water, from about 1 wt % to about 10 wt % of alkane impurities, and about 2 wt % or less of aldehyde impurities based on the total weight of the overhead.

The overhead stream is condensed and separated in a decanter to a light, aqueous phase and a heavy, organic phase. The heavy, organic phase comprises predominantly methyl iodide (greater than 50%) and the aldehyde impurity. The light, aqueous phase comprises predominantly water (greater than 50%), acetic acid, and methyl acetate. The aqueous phase is usually recycled to the reactor or to the light ends distillation.

According to the method of the invention, at least a portion of the heavy, organic phase is extracted with a polyol to remove the aldehydes. Preferably, about 5% to 100% of the heavy, organic phase is extracted with a polyol. More preferably, about 5% to about 50% of the heavy, organic phase is extracted with a polyol. The extracted, heavy, organic phase is then optionally directed to the reactor or to the light ends distillation column. The polyol which contains the aldehydes can be subjected to separation; the resulted aldedydes can be disposed and the polyol can be recycled and reused.

Suitable polyols include those which form separate phases with methyl iodide. Preferably, the polyols have hydroxyl functionality greater than or equal to 2, including glycols, triols, polyether polyols, the like, and mixtures thereof. Examples of glycols include ethylene glycol, propylene glycol, 1,4-butanediol, 1,3-butanediol, 1,5-pentanediol, 1,6-hexanediol, 2-methyl-1,3-propanediol, 2,2-dimethyl-1,3-propanediol, cyclohexane-1,4-dimethanol, and neopentyl glycol, the like, and mixtures thereof. Glycerol is an example of suitable triols. Polyether polyols include polyethylene glycol, polypropylene glycol, polybutylene glycol, the like, and mixtures thereof. Polyethers also include glycol ethers which have one or more ether linkages, such as diethylene glycol, triethylene glycol, dipropylene glycol, tripropylene glycol, the like, and mixtures thereof.

Preferably, the polyol is used in volume ratio to the methyl iodide solution or the heavy, organic phase within the range of 0.1 to 10, more preferably within the range of 0.2 to 5.

Preferably, the extraction is performed at a temperature within the range of 20° C. to 135° C. More preferably, the extraction is performed at a temperature within the range of 20° C. to 50° C.

The extraction can be performed in any suitable vessels or equipment. An example of suitable extraction equipment is decanter. The polyol and the methyl iodide solution can be mixed in a decanter. After the phase separation, the light, polyol phase can be decanted from the decanter. The extracted heavy, methyl iodide phase can be used according to the above discussion.

If the extracted heavy, methyl iodide phase contains a small amount of polyol, it is desirable to remove the polyol from the methyl iodide phase, for example, by distillation before the methyl iodide phase is recycled to the carbonylation reactor.

The following examples merely illustrate the invention. Those skilled in the art will recognize many variations that are within the spirit of the invention and scope of the claims.

EXAMPLE 1

A methyl iodide solution containing 4.1 wt % of acetaldehyde is added to a flask at room temperature (25° C.). Ethylene glycol is then added to the flask at a volume ratio of ethylene glycol/methyl iodide solution of 0.07/1. The solutions are not stirred and two phases appear: the methyl iodide phase on the bottom and ethylene glycol phase on the top. An ATR (attenuated total reflectance) infrared probe, coupled via optic conduit to an infrared spectrometer, is inserted into the methyl iodide phase. The absorption of an infrared signal of acetaldehyde at 1724 cm$^{-1}$ is monitored. The acetaldehyde concentration in the methyl iodide phase is decreased by about 27% within 20 minutes.

EXAMPLE 2

Example 1 is repeated except the volume ratio of ethylene glycol/methyl iodide solution is 0.13/1. The acetaldehyde concentration in the methyl iodide phase is decreased by 33% within 20 minutes.

EXAMPLE 3

Example 1 is repeated except the volume ratio of ethylene glycol to methyl iodide solution is 0.36/1. The acetaldehyde concentration in the methyl iodide phase is decreased by 39% within 20 minutes.

EXAMPLE 4

An aliquot of a methyl iodide solution containing 4.2 wt % of acetaldehyde and an aliquot of ethylene glycol are added to a vial. The volume ratio of ethylene glycol/methyl iodide solution is 0.5/1. The vial is capped and briefly shaken by hand. Subsequent to shaking, phase separation quickly takes place. Subsequent to phase separation, the bottom methyl iodide phase is immediately sampled by a syringe equipped with a long needle and an aliquot is analyzed by the infrared probe described in Example 1. The acetaldehyde concentration in the methyl iodide phase is decreased by 35%.

EXAMPLE 5

Example 4 is repeated except 1,4-butanediol, rather than ethylene glycol, is used and that the volume ratio of 1,4-butanediol/methyl iodide solution is 0.4/1. The acetaldehyde concentration in the methyl iodide phase is decreased by 35%.

EXAMPLE 6

Example 4 is repeated except 2-methyl-1,3-propanediol, rather than ethylene glycol, is used and the volume ratio of 2-methyl-1,3-propanediol/methyl iodide solution is 0.4/1. The acetaldehyde concentration in the methyl iodide phase is decreased by 43.5%.

EXAMPLE 7

Example 4 is repeated except glycerol, rather than ethylene glycol, is used and the volume ratio of 2-methyl-1,3-propanediol/methyl iodide solution is 0.4/1. The acetaldehyde concentration in the methyl iodide phase is decreased by 13%.

EXAMPLE 8

Example 4 is repeated except the methyl iodide solution is a decanter heavy phase type from a methanol carbonylation, which contains 4.2 wt % acetaldehyde, 10 wt % methyl acetate, 5.4 wt % acetic acid and 80.4 wt % methyl iodide. The volume ratio of methyl iodide solution/ethylene glycol is 1/1. The acetaldehyde concentration in the methyl iodide phase is decreased by 34%.

EXAMPLE 9

Example 8 is repeated except 1,3-propanediol, rather than ethylene glycol, is used. The acetaldehyde concentration in the methyl iodide phase is decreased by 25%.

EXAMPLE 10

Example 8 is repeated except 1,4-butanediol, rather than ethylene glycol, is used. The acetaldehyde concentration in the methyl iodide phase is decreased by 37%.

EXAMPLE 11

Example 8 is repeated except glycerol, rather than ethylene glycol, is used. The acetaldehyde concentration in the methyl iodide phase is decreased by 27%.

We claim:

1. A method for removing an aldehyde from a methyl iodide solution, said method comprising extracting the aldehyde from the solution with a polyol.

2. The method of claim 1, wherein the polyol is a glycol.

3. The method of claim 1, wherein the polyol is glycerol.

4. The method of claim 1, wherein the aldehyde is acetaldehyde.

5. The method of claim 1, wherein the methyl iodide solution is a decanter heavy phase from an acetic acid production process.

6. The method of claim 5, wherein the decanter heavy phase comprises from 60 wt % to 90 wt % of methyl iodide, 1 wt % to 10 wt % of acetic acid, 2 wt % to 15 wt % of methyl acetate, 1 wt % to 10 wt % of an alkane, 0.01 wt % to 1 wt % of water, and 0.1 wt % to 5 wt % of the aldehyde.

7. The method of claim 1, wherein the methyl iodide solution and the polyol are mixed in a volume ratio within the range of 0.1/1 to 10/1.

8. The method of claim 1, where the methyl iodide solution and the polyol are mixed in a volume ratio within the range of 0.2/1 to 5/1.

9. A method for removing an aldehyde from acetic acid, said method comprising:
   (a) reacting methanol and carbon monoxide in the presence of a carbonylation catalyst, a catalyst stabilizer, methyl iodide, water and methyl acetate to produce an acetic acid stream containing an aldehyde;
   (b) flashing at least a portion of the acetic acid stream into a vapor stream comprising acetic acid, water, methanol, methyl acetate, methyl iodide and the aldehyde, and a liquid stream comprising the catalyst and the catalyst stabilizer;
   (c) separating the vapor stream by distillation into a product stream comprising acetic acid and water, and an overhead stream comprising methyl iodide, water, methyl acetate, and the aldehyde;
   (d) condensing and separating the overhead stream in a decanter into a light, aqueous phase comprising water, acetic acid, and methyl acetate, and a heavy, organic phase comprising methyl iodide and the aldehyde; and
   (e) extracting the aldehyde from the heavy, organic phase with a polyol.

10. The method of claim 9, wherein the catalyst is a rhodium catalyst.

11. The method of claim 9, wherein the catalyst stabilizer is triphenylphosphine oxide.

12. The method of claim 9, wherein the concentration of water in step (a) is within the range of 4 wt % to 10 wt % of the reaction mixture.

13. The method of claim 9, wherein the aldehyde is acetaldehyde.

14. The method of claim 9, wherein the polyol is a glycol.

15. The method of claim 9, wherein the polyol is glycerol.

16. The method of claim 9, wherein the heavy, organic phase of step (d) comprises from 60 wt % to 90 wt % of methyl iodide, 1 wt % to 10 wt % of acetic acid, 2 wt % to 15 wt % of methyl acetate, 1 wt % to 10 wt % of an alkane, 0.01 wt % to 1 wt % of water, and 0.1 wt % to 5 wt % or less of the aldehyde.

17. The method of claim 9, which comprises recycling the polyol-extracted heavy, organic phase from step (e) to the reaction of step (a).

* * * * *